United States Patent
Moise et al.

(10) Patent No.: US 9,989,670 B2
(45) Date of Patent: Jun. 5, 2018

(54) OPTICAL AND ELECTRICAL SENSING OF A MULTIPHASE FLUID

(71) Applicant: Schlumberger Technology Corporation, Sugar land, TX (US)

(72) Inventors: Stefan Iulian Moise, Paris (FR); Olivier Amsellem, Le Plessis Robinson (FR); Pierre Vigneaux, Paris (FR); Caroline Stephan Rivas, Paris (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 160 days.

(21) Appl. No.: 14/717,981

(22) Filed: May 20, 2015

(65) Prior Publication Data

US 2015/0338547 A1    Nov. 26, 2015

(30) Foreign Application Priority Data

May 20, 2014    (EP) .................................... 14290149

(51) Int. Cl.
| | |
|---|---|
| *G01N 33/28* | (2006.01) |
| *G01V 8/02* | (2006.01) |
| *E21B 47/10* | (2012.01) |
| *G01N 27/07* | (2006.01) |
| *G01N 9/00* | (2006.01) |
| *G01N 21/41* | (2006.01) |
| *G01N 21/84* | (2006.01) |
| *G01F 1/74* | (2006.01) |

(52) U.S. Cl.
CPC .............. *G01V 8/02* (2013.01); *E21B 47/102* (2013.01); *G01N 9/00* (2013.01); *G01N 21/41* (2013.01); *G01N 21/84* (2013.01); *G01N 27/07* (2013.01); *G01N 33/2823* (2013.01); *G01F 1/74* (2013.01); *G01N 2021/8405* (2013.01)

(58) Field of Classification Search
CPC ... E21B 47/102; E21B 47/04; G01N 33/2823; G01N 21/00; G01N 27/02; G01N 27/07; G01N 9/00; B01D 29/085; B01D 35/02; E04D 13/0767
USPC .......................................................... 356/70
See application file for complete search history.

(56) References Cited

U.S. PATENT DOCUMENTS 5,088,324 A    2/1992 Nemeth
2002/0147447 A1*  10/2002 Long .................. A61B 18/1492
                                                    606/41

(Continued)

FOREIGN PATENT DOCUMENTS

EP        0508894        10/1992

OTHER PUBLICATIONS

Extended European Search Report issued in related EP Application No. 14290149.5 dated Nov. 26, 2014.

*Primary Examiner* — Sunghee Y Gray
(74) *Attorney, Agent, or Firm* — Michael Dae (57) ABSTRACT

Apparatus and methods for optical and electrical sensing different phases of a multiphase fluid. The apparatus includes a cylindrical member formed with an optically transparent material including a first end with a shaped tip and a second end operable to receive an optical conductor. The apparatus also includes first and second electrodes disposed on the cylindrical member operable to receive first and second electrical conductors, respectively.

14 Claims, 6 Drawing Sheets

(56) References Cited

U.S. PATENT DOCUMENTS

| | | | |
|---|---|---|---|
| 2004/0263175 A1* | 12/2004 | Chouzenoux | E21B 17/003 324/368 |
| 2005/0062429 A1* | 3/2005 | Imoto | H01J 61/06 315/94 |
| 2009/0180101 A1* | 7/2009 | Csutak | G01N 21/51 356/70 |
| 2010/0298738 A1* | 11/2010 | Felts | B05D 1/62 600/576 |
| 2011/0156581 A1* | 6/2011 | Yasuda | H01J 61/16 313/572 |
| 2011/0252899 A1* | 10/2011 | Felts | C23C 16/045 73/865.8 |
| 2012/0169225 A1* | 7/2012 | Ito | H01J 9/022 313/631 |
| 2012/0203245 A1* | 8/2012 | Imabayashi | A61N 1/0592 606/129 |
| 2013/0037623 A1* | 2/2013 | Yamaguchi | B01L 3/0268 239/11 |
| 2013/0148196 A1* | 6/2013 | Arnold | G02B 21/025 359/385 |
| 2013/0258319 A1 | 10/2013 | Schleicher et al. | |
| 2013/0312801 A1* | 11/2013 | Carroll | H01L 31/02246 136/201 |
| 2014/0333307 A1* | 11/2014 | Ahmad | E21B 49/08 324/324 |

* cited by examiner

OPTICAL AND ELECTRICAL SENSING OF A MULTIPHASE FLUID

BACKGROUND OF THE DISCLOSURE

During drilling operations for oil and gas wells, the operator may obtain downhole data, such as properties of multiphase fluids. These tasks are accomplished with downhole tools, such as a modular wireline or coiled tubing tool with evaluation capabilities. Such downhole tools may employ probes for engaging the formation and establishing fluid communication to make the measurements. The measurements may be utilized to determine what fraction of the multiphase fluid is constituted by liquid hydrocarbons, in contrast to gaseous hydrocarbons and non-hydrocarbon compositions, like water. Existing sensors for obtaining such measurements, however, cannot distinguish between the three standard components (liquid hydrocarbons, water, and gas), and/or cannot withstand the rigors of the downhole environment.

SUMMARY OF THE DISCLOSURE

The present disclosure introduces an apparatus that includes a cylindrical member formed with an optically transparent material. The cylindrical member includes a first end with a shaped tip and a second end operable to receive or otherwise optically couple with an optical conductor. Electrodes are disposed on opposing sides of the cylindrical member, for connection with corresponding electrical conductors.

The present disclosure also introduces a method in which an integrated sensor is submerged in a multiphase fluid. The integrated sensor includes a cylindrical member formed with an optically transparent material, with electrodes disposed on opposing sides of the cylindrical member. Light is directed through the cylindrical member to a shaped tip thereof. Different phases of the multiphase fluid are distinguished based on a difference between refractive indexes of the shaped tip and the different phases of multiphase fluid. The difference between the refractive indexes is determined based on reflection of the light from the shaped tip of the cylindrical member. A response of an electrical signal transmitted between the first and second electrodes is also determined. Water and oil within the multiphase fluid are distinguished based on the response.

The present disclosure also introduces a downhole tool that includes a probe conveyable within a wellbore via a conveyance. The wellbore extends from a wellsite surface to a subterranean formation. The conveyance includes an optical conductor and at least first and second electrical conductors. The probe includes an integrated sensor including a cylindrical member formed with an optically transparent material including a first end with a shaped tip and a second end operable to receive an optical conductor. The integrated sensor also includes first and second electrodes disposed on the cylindrical member for connection with the first and second electrical conductors, respectively.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It should be noted that, in the development of an actual implementation within the scope of the present disclosure, numerous implementation-specific decisions may be made to achieve predetermined goal, such as compliance with system- and business-related constraints, which may vary from one implementation to another. However, a person having ordinary skill in the art will appreciate that such development may be complex and time consuming, but would nevertheless be a routine undertaking for those of ordinary skill in the art having the benefit of the present disclosure.

Example implementations within the scope of the present disclosure are described below with reference to the accompanying drawings. Numerous details are set forth below to provide a more thorough understanding of various aspects of the present disclosure. However, a person having ordinary skill in the art will appreciate that the example implementations disclosed herein may be practiced without some of these details. In other instances, well-known features may not be described in detail, such as may avoid complicating the following description.

Various terminology and phraseology are used herein for descriptive purposes, and thus may not be limiting in scope. Language such as "including," "comprising," "having," "containing," and "involving," and variations thereof, is intended to be broad and encompass the subject matter listed thereafter, equivalents, and additional subject matter not explicitly recited.

In addition, the present disclosure may repeat reference numerals and/or letters in the various example implementations. This repetition is for simplicity and clarity, and does not in itself dictate a relationship between the various implementations, embodiments, and/or configurations described below.

Implementations within the scope of the present disclosure may relate generally, but not by way of limitation, to an apparatus and method for discriminating among the phases of a surrounding, perhaps moving, multiphase fluid containing a phase (e.g., a liquid phase) that may include oil and/or water, and another phase (e.g., a gaseous phase) having a refractive index that is different from the liquid phase.

Figure 1:
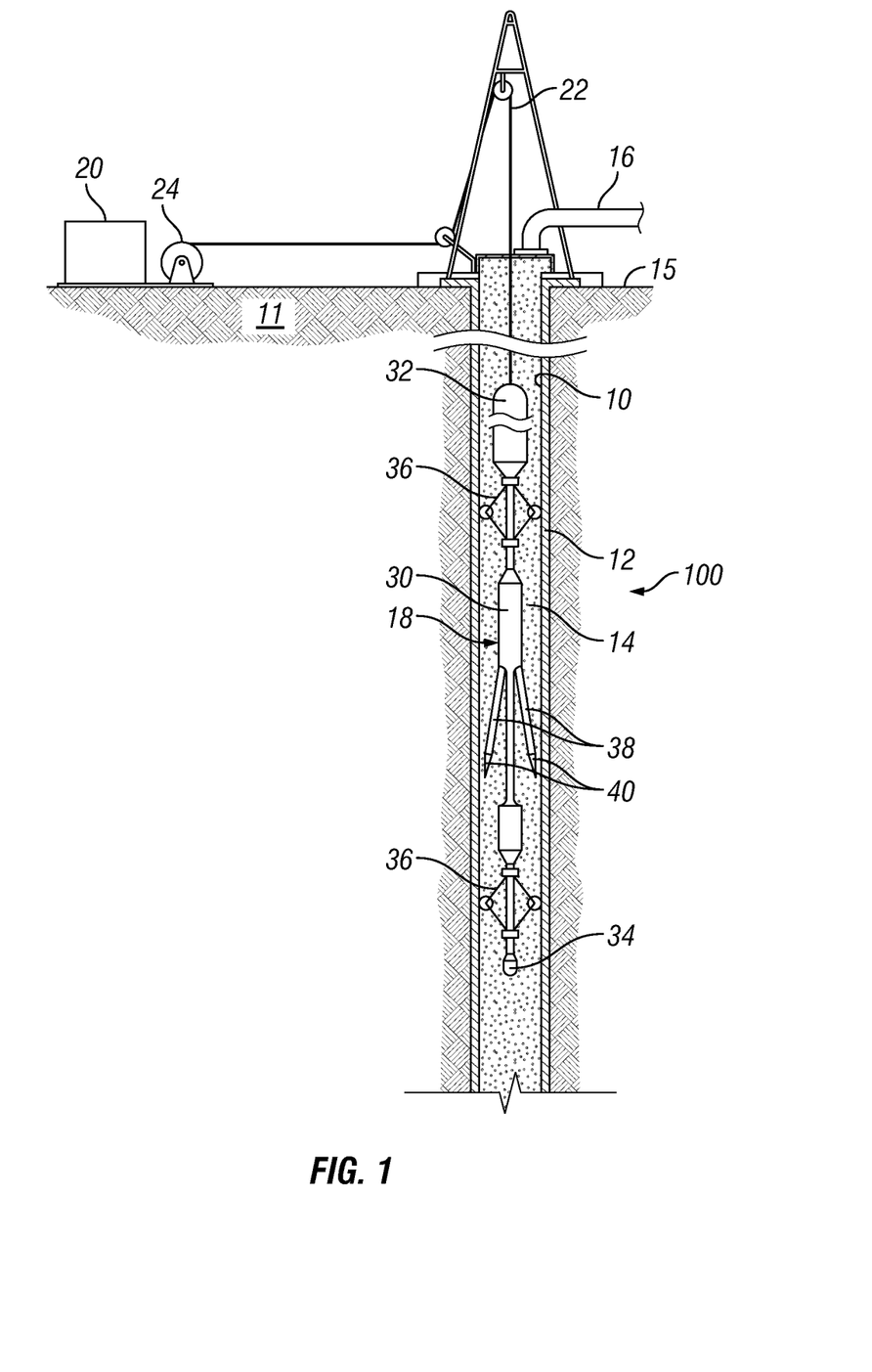
FIG. 1 is a schematic view of at least a portion of apparatus according to one or more aspects of the present disclosure.

FIG. 1 is a schematic view of a downhole tool 100 according to one or more aspects of the present disclosure. The downhole tool 100 is depicted in FIG. 1 as being conveyed within a well 10 extending into a subterranean formation 11 lined internally with a tubular structure (e.g., production tubing and/or casing) 12 through which a multiphase fluid 14 flows towards a wellsite surface 15. The multiphase fluid 14 comprises water, oil, and gas. The oil and/or gas may comprise one or more hydrocarbon components, such as methane, ethane, propane, butane, pentane, hexane, and/or others. Various ducting 16 at the surface 15 may transport the multiphase fluid 14 to a storage installation and/or other surface equipment (not shown). The downhole tool 100 is or comprises a logging tool 18 suitable for being displaced within the tubular structure 12 to perform measurements at different depths. The downhole tool 100 also comprises or operates in conjunction with a surface unit 20, including a system for exploiting information delivered by the logging tool 18. The logging tool 18 is suspended from the end of a cable 22 whose opposite end is wound onto a winch 24.

The logging tool 18 includes an elongated body 30 of which top and bottom ends are respectively connected to an electronics section 32 and to a nose 34. Positioning members 36 such as centralizers are placed immediately above and below the elongated body 30 so as to position the elongated body 30 inside the tubular structure 12 when a measurement is to be performed. In the example shown, the positioning members 36 serve to place the elongated body 30 on an axis of the tubular structure 12. However, other types of positioning members may also or instead be utilized, perhaps including to urge the elongated body 30 and/or another portion of the logging tool 18 against the tubular structure 12.

The logging tool 18 may comprise one or more hinged arms 38 each pivotally mounted about axes that may be orthogonal to a longitudinal axis of the logging tool 18. Each hinged arm 38 may be movable between a retracted position against the elongated body 30 and a deployed position as shown in FIG. 1. The retracted position may be used while the logging tool 18 is being displaced between two measurement stations and/or run into and/or out of the well 10. In contrast, the hinged arms 38 that carry measurement sondes (or probes) 40 at ends thereof are placed in the deployed positions when a measurement is to be performed. One or more hydraulic, electrical, mechanical, and/or other types of motors, servos, and/or other types of actuators (not shown) may be operable to transition the hinged arms 38 between the retracted and deployed positions.

Each probe 40 comprises an integrated sensor operable to measure different physical characteristics of the multiphase fluid 14 at a single location. The physical characteristics may be selected so that the integrated sensor is operable to discriminate between the phases contained in the multiphase fluid 14. For example, where the multiphase fluid 14 includes a continuous water phase containing oil and gas, the integrated sensor is operable to distinguish (1) between oil and gas (or between a liquid phase and a gaseous phase) and (2) between oil and liquid water.

The integrated sensor introduced herein is formed with a hybrid optical and electrical sensor to differentiate phases of surrounding multiphase fluids at the same location and time. The probe including the integrated sensor may be employed in downhole applications, but may also be used for surface measurements. The integrated sensor is constructed around an optically transparent cylindrical member terminated at a first end with a shaped tip. The shaped tip of the optical sensor (of the integrated sensor) is realized by a termination geometry, which, without limitation, may be substantially asymmetrically, conically, biconically, conically rounded or rounded shaped, or may present combinations of these geometries.

The electrical sensor of the integrated sensor is constructed with at least two electrodes (e.g., metal electrodes) deposited on the optically transparent cylindrical member. The geometry of the electrodes may vary. Thus, a probe with the integrated sensor may discriminate directly between the phases of a multiphase fluid such as a fluid containing a water, oil, and/or gas. As an example, a multiphase fluid may contain water, oil, and gas, which have respective refractive indices of about 1.33, about 1.5, and about 1. Under such circumstances, the refractive index of the optically transparent material from which the integrated sensor is made may be greater than about 1.45.

The integrated sensor can withstand the rigors of the temperature and pressure variations in downhole applications or other challenging environments. To ensure that the integrated sensor withstands the pressure and temperature variations of the surrounding multiphase fluid (and downhole environment), and to lessen or avoid any risk of fluid infiltrating into the interfaces between the various layers thereof, parts of the integrated sensor may be interconnected by gluing or by melting a protective coating (e.g., a protective metal coating) thereon.

Figure 2:
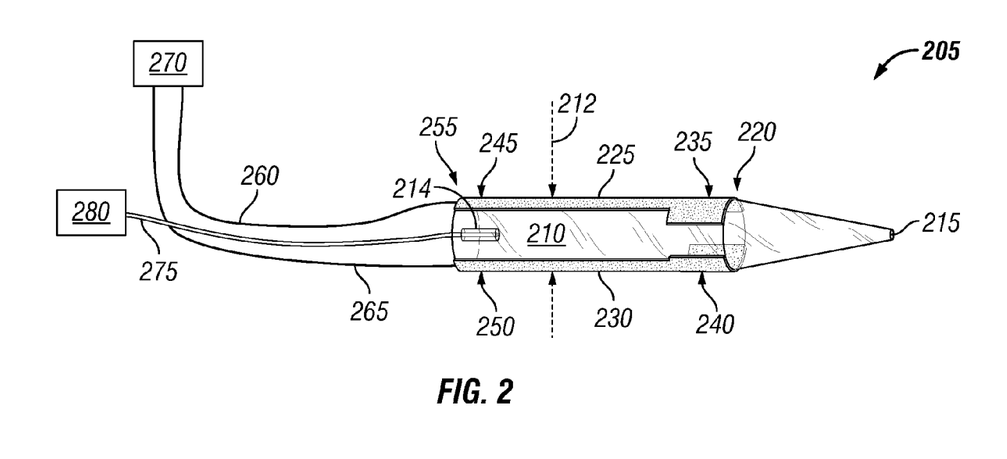
FIGS. 2 and 3 are lateral and end views, respectively, of at least a portion of apparatus according to one or more aspects of the present disclosure.
Figure 3:
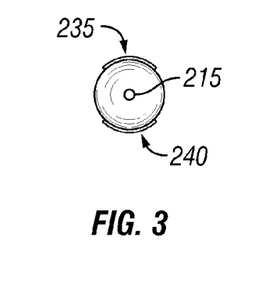

FIGS. 2 and 3 illustrate lateral and end views, respectively, of an integrated sensor 205 according to one or more aspects of the present disclosure. The integrated sensor 205 includes a cylindrical member 210 formed with an optically transparent material, such as sapphire and/or other optically transparent materials with a refractive index greater than about 1.45. The cylindrical member 210 forms at least a portion of an optical sensor for the integrated sensor 205. The cylindrical member 210 includes a shaped tip 215 at a first end 220 thereof, such as a substantially conical shaped tip. The cylindrical member 210 may have a diameter 212 ranging between about three centimeters and about 10 centimeters, such as about five centimeters.

The integrated sensor 205 also includes first and second electrodes (e.g., metal electrodes) 225, 230 disposed on the cylindrical member 210. The first and second electrodes 225, 230 form at least a portion of an electrical sensor for the integrated sensor 205. The first and second electrodes 225, 230 each have a first surface 235, 240 proximate the first end 220 of the cylindrical member 210 and a second surface 245, 250 located between the first surfaces 235, 240 and a second end 255 of the cylindrical member 210. The first surfaces 235, 240 may have a larger surface area than the second surfaces 245, 250, such as to bring a measurement of resistivity of surrounding multiphase fluid closer to the shaped tip 215 of the cylindrical member 210. The first and second surfaces 235, 240, 245, 250 of the respective first and second electrodes 225, 230 may be deposited onto the cylindrical member 210 via physical vapor deposition and/or other deposition techniques, perhaps to a thickness ranging between about one micron and about 10 microns, such as about five microns. One example of such deposition is a first deposited layer of titanium, a second deposited layer of gold and a third deposited layer of nickel. However, tungsten, chrome, and/or other metals may also or instead be utilized. As opposed to metal sleeves that fit over the cylindrical member 210, the thin first and second surfaces 235, 240, 245, 250 of the respective first and second electrodes 225, 230 may lessen or avoid contaminating the surrounding multiphase fluids and/or substantially disturbing the flow of the surrounding multiphase fluids.

The first and second electrodes 225, 230 are coupled (e.g., soldered) to an end of first and second electrical conductors (e.g., metal wires) 260, 265, respectively, proximate the second end 255 of the cylindrical member 210. Another end of the first and second electrical conductors 260, 265 is connected to an electrical source and an electrical receiver, which are collectively designated by reference numeral 270 in FIG. 2. The first and second electrodes 225, 230 are operable to distinguish between water and oil. An electrical signal (e.g., a voltage) produced by the electrical source and electrical receiver 270 is applied between the first and second electrodes 225, 230 via the first and second electrical conductors 260, 265 to measure a resistivity of the multiphase fluid surrounding the integrated sensor 205. At least an order of magnitude change is expected between the resistivity of water and oil. Therefore, a greater current flow between the first and second electrodes 225, 230 resulting from application of the voltage, and detected by the electrical receiver in the electrical source and electrical receiver 270, indicates a presence of water, or at least a higher concentration of water relative to oil. As a result, the electrical sensor of the integrated sensor 205 can facilitate a process to distinguish water from oil.

An optical conductor (e.g., a fiber such as a silica fiber) 275 is also terminated and/or otherwise coupled to the second end 255 of the cylindrical member 210. For example, the optical conductor 275 may be coupled to the cylindrical member 210 by drilling, etching, and/or otherwise forming a hole 214 in the second end 255 of the cylindrical member 210, inserting the end of the optical conductor 275 into the hole 214, and using an adhesive such as an epoxy to retain the end of the optical conductor 275 in the hole 214. Another end of the optical conductor 275 is connected to a light source and photodetector, collectively designated in FIG. 2 by reference numeral 280.

The optical conductor 275 may be formed as a part of a cable that can be a coaxial cable with a metal coating. The first and second electrical conductors 260, 265 and the optical conductor 275 may be routed generally parallel from the integrated sensor 205 to the respective electrical source and an electrical receiver 270 and light source and photodetector 280. Light produced by the light source and photodetector 280 (for example, the light source portion, such as a laser diode) may thus be directed by the optical conductor 275 into the optically transparent material of the cylindrical member 210 and then travel to the shaped tip 215. A portion of the light leaves the shaped tip 215 through refraction. Remaining light is reflected back through the cylindrical member 210 and is returned to the photodetector (in the light source and photodetector 280) through the optical conductor 275. The quantity of photons in the reflected rays returned through the optical conductor 275 is strongly dependent on the difference of refractive indexes between the shaped tip 215 and the multiphase fluid surrounding the shaped tip 215. The refractive index of the optically transparent material of the cylindrical member 210 and shaped tip 215 may be closer to the refractive index of most liquids than to the refractive index of most gases. Therefore, more light is expected to be reflected at a surface of the shaped tip 215 in a gaseous environment. This process is used to distinguish a gas from a liquid.

Figure 4:
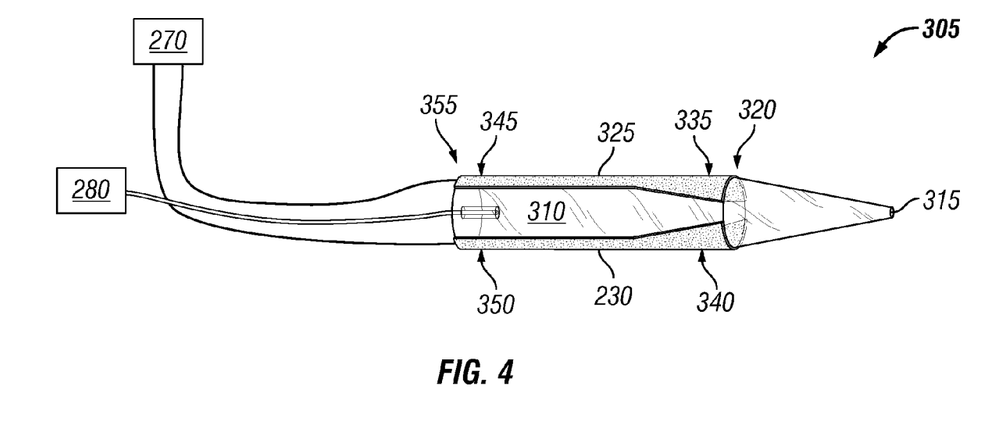
FIGS. 4 and 5 are lateral and end views, respectively, of at least a portion of apparatus according to one or more aspects of the present disclosure.
Figure 5:
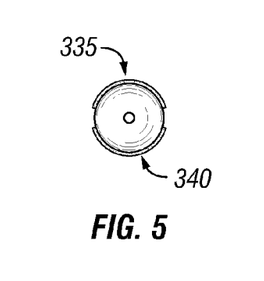

FIGS. 4 and 5 are lateral and end views, respectively, of another implementation of the integrated sensor 205 shown in FIGS. 2 and 3, designated herein by reference numeral 305, according to one or more aspects of the present disclosure. The integrated sensor 305 includes many analogous features to the integrated sensor 205 illustrated in FIGS. 2 and 3 and, as such, the analogous features will not be repeated herein. In the implementation depicted in FIGS. 4 and 5, however, first and second electrodes 325, 330 disposed on a cylindrical member 310 formed with an optically transparent material with a shaped tip 315 are formed with another geometry. The first and second electrodes 325, 330 each have a first surface 335, 340 proximate a first end 320 of the cylindrical member 310 and a second surface 345, 350 located between the first surface 335, 340 and a second end 355 of the cylindrical member 310. The first surface 335, 340 of the respective first and second electrodes 325, 330 is tapered from the first end 320 of the cylindrical member 310 toward the second surface 345, 350 of the respective first and second electrodes 325, 330. The tapered structure of the first surfaces 335, 340 further brings a measurement of resistivity of a surrounding multiphase fluid closer to the shaped tip 315 of the cylindrical member 310.

Figure 6:
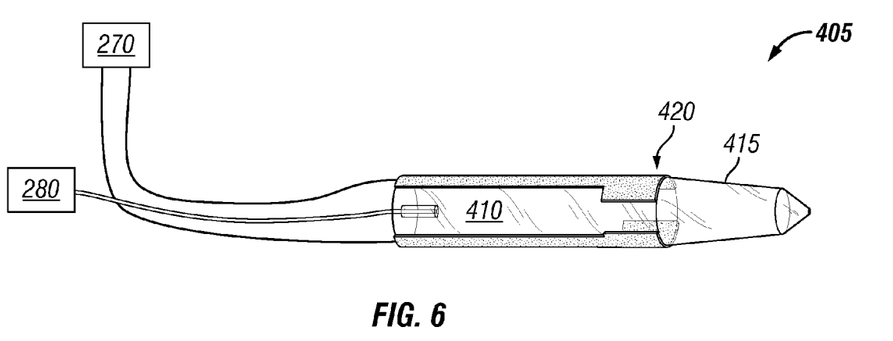
FIG. 6 is a lateral view of at least a portion of apparatus according to one or more aspects of the present disclosure.

FIG. 6 is a lateral view of another implementation of the integrated sensor 205 shown in FIGS. 2 and 3, designated herein by reference numeral 405, according to one or more aspects of the present disclosure. The integrated sensor 405 includes many analogous features to the integrated sensor 205 illustrated in FIGS. 2 and 3 and, as such, the analogous features will not be repeated herein. In the implementation depicted in FIG. 6, however, the integrated sensor 405 includes a cylindrical member 410 formed with an optically transparent material with a substantially biconical shaped tip 415 at a first end 420 thereof. The optical characteristics of a substantially biconical shaped tip 415 may be beneficial depending on the application for the integrated sensor 405.

The geometry of the tip may have a direct impact on sensing performance, such that a first geometry may be utilized for a first environment to optimize performance, for example, while a second geometry may be utilized for a different, second environment, whether to optimize performance and/or otherwise. Thus, the examples provided herein are just that, and a person having ordinary skill in the art will readily recognize that other implementations may also fall within the scope of the present disclosure.

Figure 7:
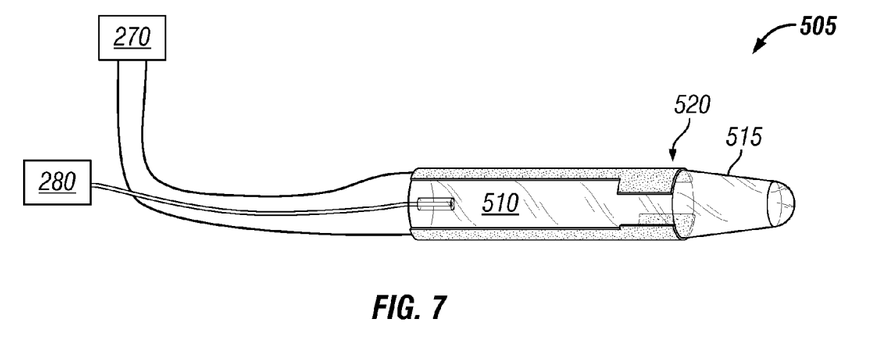
FIG. 7 is a lateral view of at least a portion of apparatus according to one or more aspects of the present disclosure.

FIG. 7 is a lateral view of another implementation of the integrated sensor 205 shown in FIGS. 2 and 3, designated herein by reference numeral 505, according to one or more aspects of the present disclosure. The integrated sensor 505 includes many analogous features to the integrated sensor 205 illustrated in FIGS. 2 and 3 and, as such, the analogous features will not be repeated herein. In the implementation depicted in FIG. 7, however, the integrated sensor 505 includes a cylindrical member 510 formed with an optically transparent material with a substantially conical rounded shaped tip 515 at a first end 520 thereof. The optical characteristics of a substantially conical rounded shaped tip 515 may be beneficial depending on the application for the integrated sensor 505.

Figure 8:
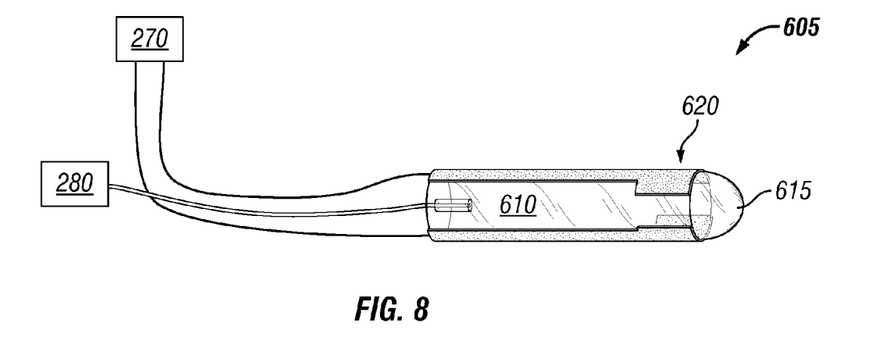
FIG. 8 is a lateral view of at least a portion of apparatus according to one or more aspects of the present disclosure.

FIG. 8 is a lateral view of another implementation of the integrated sensor 205 shown in FIGS. 2 and 3, designated herein by reference numeral 605, according to one or more aspects of the present disclosure. The integrated sensor 605 includes many analogous features to the integrated sensor 205 illustrated in FIGS. 2 and 3 and, as such, the analogous features will not be repeated herein. In the implementation depicted in FIG. 8, however, the integrated sensor 605 includes a cylindrical member 610 formed with an optically transparent material with a substantially rounded shaped tip 615 at a first end 620 thereof. The optical characteristics of a substantially rounded shaped tip 615 may be beneficial depending on the application for the integrated sensor 605.

Figure 9:
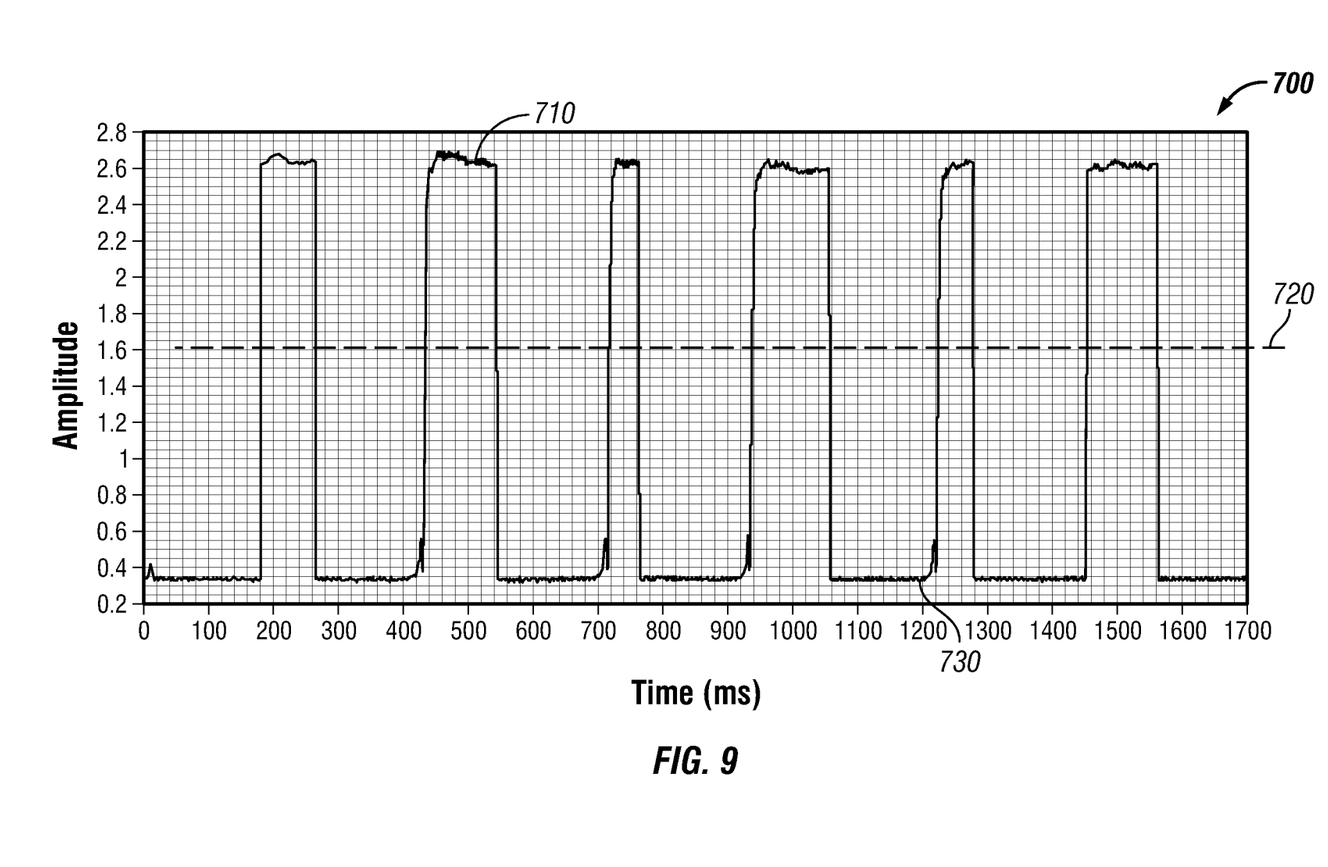
FIG. 9 is a waveform diagram demonstrating a reflectance measurement according to one or more aspects of the present disclosure.

FIG. 9 is a waveform diagram demonstrating a reflectance measurement differentiating a gaseous phase from a liquid phase (e.g., water/oil) according to one or more aspects of the present disclosure. Amplitude of a signal (e.g., a voltage signal) 700 after photovoltaic conversion by a photodetector is illustrated on the vertical axis, and time is illustrated on the horizontal axis. The amplitude of the voltage signal 700 generated in a gaseous environment (e.g., at a point 710) is higher than a predetermined threshold 720, triggering detection of a gaseous phase. In water and oil environments, the amplitude of the voltage signal 700 remains lower (e.g., at a point 730) than the predetermined threshold 720. Thus, the amplitude of the voltage signal 700 represents a distinction between gaseous and liquid phases.

Figure 10:
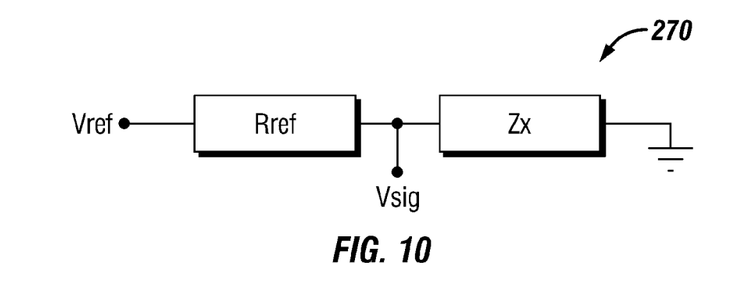
FIG. 10 is a block diagram of at least a portion of apparatus according to one or more aspects of the present disclosure.

FIG. 10 is a block diagram of an example implementation of the electrical source and electrical receiver 270 shown in FIG. 2 according to one or more aspects of the present disclosure. The electrical source and electrical receiver makes an electrical measurement to sense resistivity of a multiphase fluid surrounding an integrated sensor by applying an electrical signal (e.g., a voltage signal) between first and second electrodes (see, e.g., FIGS. 2 and 3). The electrical resistivity of water, which is much lower than the electrical resistivity of oil, allows a greater current (a response or a return electrical signal) to flow between the first and second electrodes. A current-to-voltage converter in the electrical source and electrical receiver that is electrically coupled to the first and second electrodes via first and second electrical conductors, respectively, generates a signal shape generally similar to the waveform presented in FIG. 9. The first and second electrodes are represented by an impedance Zx, which is connected to the electrical source and electrical receiver 270 over two electrical conductors, such as the first and second electrical conductors described above. A reference resistance represented by a resistor Rref is coupled between the impedance Zx and a reference voltage Vref. The reference voltage Vref may be a direct current ("dc") voltage of either polarity, perhaps with a grounded positive conductor to reduce electrolytic corrosion of an accidentally exposed portion of either conductor. The reference voltage Vref may also or instead be a low frequency (e.g., 60 hertz) alternating current ("ac") voltage.

The impedance Zx may be represented as Zx=(Vsig*Rref)/(Vref−Vsig), wherein Vsig represents an output voltage signal. The reference voltage Vref (an electrical signal) is thus applied to the first and second electrodes coupled in series with the resistor Rref. When the resistivity of the surrounding multiphase fluid represented by the impedance Zx is high, the current flowing through the resistor Rref is low and the output voltage signal Vsig is high and close to the level of the reference voltage Vref. If the impedance Zx is low, the output voltage signal Vsig will also be low. Between water and oil at least an order of magnitude in the resistivity change is expected. Therefore, the dynamic level of the output voltage signal Vsig may be indicative, resulting in low voltage signals Vsig corresponding to water and higher voltage signals Vsig corresponding to oil. However, this represents merely an example of acquisition scheme, such that other schemes may also or instead be utilized to measure impedance, such as may utilize bridge imbalance, resonators, and/or others.

Figure 11:
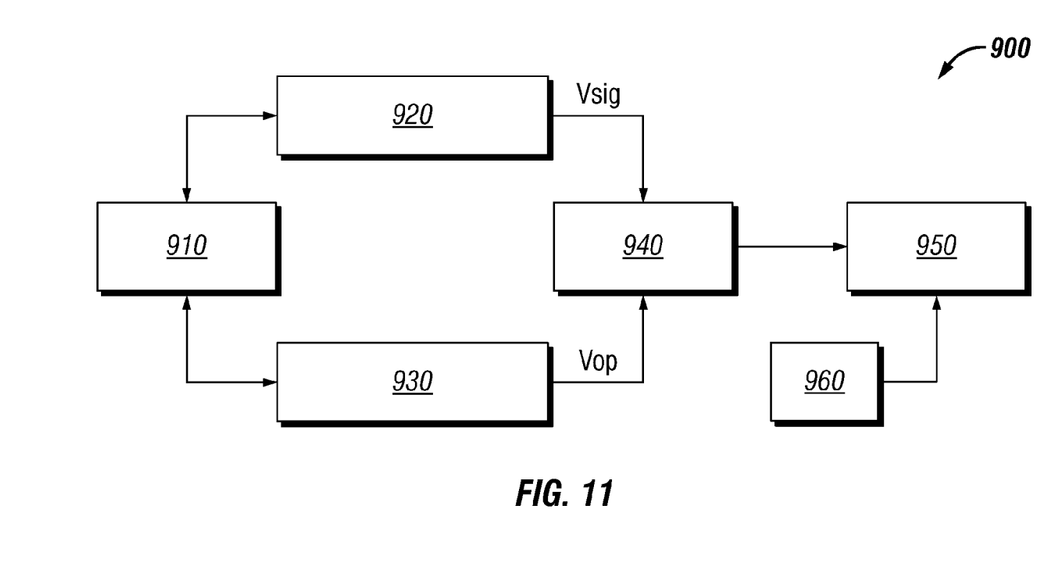
FIG. 11 is a block diagram of at least a portion of apparatus according to one or more aspects of the present disclosure.

FIG. 11 is a block-diagram view of portions of a probe including an integrated sensor 910 and control system 900 according to one or more aspects of the present disclosure. The integrated sensor 910 is coupled to an electrical source and electrical receiver 920 via electrical conductors. The electrical source and electrical receiver 920 provides an electrical measurement signal Vsig as described above. The integrated sensor 910 is also coupled to a light source and photodetector 930 via an optical conductor. The light source and photodetector 930 provides an optical measurement signal Vop as described above. The electrical and optical measurement signals Vsig, Vop are thereafter provided to an analog-to-digital converter 940 to produce a digital version of the respective signals. The digital versions of the electrical and optical measurement signals Vsig, Vop are then provided to a processor 950 for further processing.

The processor 950 in combination with a memory 960 processes each of the digital versions of the electrical and optical measurement signals Vsig, Vop to obtain respective binary signals having values greater or less than a predetermined threshold or value. Based thereon, the processor 950 can distinguish water from oil from the digital version of the electrical measurement signal Vsig and can distinguish a gas from a liquid from the digital version of the optical measurement signal Vop. Thus, the processor 950 is operable to determine the phase of the multiphase fluid surrounding the integrated sensor 910, and is also operable to determine other properties of the fluid such as, without limitation, a flow rate of the detected phase in the location of the integrated sensor 910. It may also be observed that although the integrated sensor 910 has been described in the environment of an oil well, other applications entailing obtaining a phase of a multiphase fluid not disposed in an oil well are also within the scope of the present disclosure.

The processor 950 and/or other components of the control system 900 may be implemented with one or a plurality of processors of various types suitable to the local application environment, and may include one or more of general-purpose computers, special purpose computers, microprocessors, digital signal processors ("DSPs"), field-programmable gate arrays ("FPGAs"), application-specific integrated circuits ("ASICs"), and processors based on a multi-core processor architecture, as non-limiting examples. The memory 960 may also include one or more memories of various types suitable to the local application environment, and may be implemented using various suitable volatile or nonvolatile data storage technology such as a semiconductor-based memory device, a magnetic memory device and system, an optical memory device and system, fixed memory, and removable memory, among other examples. The programs stored in the memory may include program instructions or computer program code that, when executed by an associated processor, enable the integrated sensor 910 and control system 900 to perform tasks as described herein. Additionally, modules such as the electrical source and electrical receiver 920 may include a transceiver operable to allow the same to communicate with another system of a downhole tool.

The modules of the control system 900 may be implemented in accordance with hardware (embodied in one or more chips including an integrated circuit such as an application specific integrated circuit), or may be implemented as software or firmware for execution by a processor. In particular, in the case of firmware or software, the embodiment can be provided as a computer program product including a computer readable medium or storage structure embodying computer program code (i.e., software or firmware) thereon for execution by the processor.

FIG. 10 is a flow-chart diagram of at least a portion of a method (1000) of distinguishing phases of a multiphase fluid according to one or more aspects of the present disclosure. The method (1000) includes submerging (1010) an integrated sensor in a multiphase fluid. The integrated sensor includes a cylindrical member formed with an optically transparent material and first and second electrodes disposed on the cylindrical member, and may be substantially similar to the apparatus shown in one or more of FIGS. 1-8.

Figure 12:
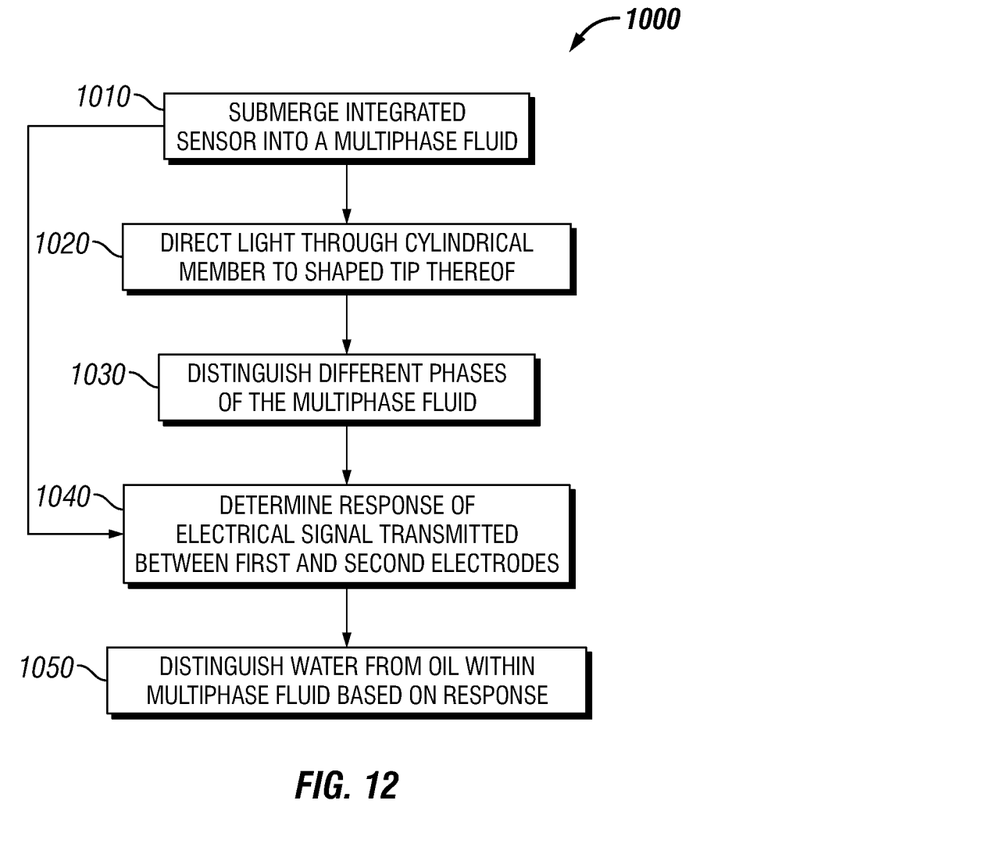
FIG. 12 is a flow-chart diagram of at least a portion of a method according to one or more aspects of the present disclosure.

Light is then directed (1020) through the cylindrical member to a shaped tip thereof. Different phases of the multiphase fluid are then distinguished (1030) based on a difference between refractive indexes of the shaped tip and the different phases of multiphase fluid. The difference between the refractive indexes is determined based on reflection of the light from the shaped tip of the cylindrical member. In accordance therewith, the reflection may be converted to an electrical signal, and distinguishing (1030) different phases of the multiphase fluid may include comparing an amplitude of the electrical signal to a predetermined threshold. If the amplitude is greater than the predetermined threshold, then a gas is identified in the multiphase fluid. If the amplitude is less than the predetermined threshold, then a liquid is identified in the multiphase fluid.

A response of an electrical signal transmitted between the first and second electrodes may then be determined (1040), and water and oil within the multiphase fluid may then be distinguished (1050) based on the response. In accordance therewith, a value of the response can be compared to a predetermined value. If the value of the response is greater than the predetermined value, then water is identified in the multiphase fluid. If the value of the response is less than the predetermined value, then oil is identified in the multiphase fluid.

In view of all of the above, including the figures, a person having ordinary skill in the art should readily recognize that the present disclosure introduces an apparatus (e.g., an integrated sensor employable as or with a probe) that includes a cylindrical member formed with an optically transparent material including a first end with a shaped tip and a second end operable to receive an optical conductor. The shaped tip may be substantially conical, biconical, conically rounded, or rounded. The optically transparent material may include sapphire. The optically transparent material may have an index of refraction greater than about 1.45. The apparatus also includes first and second electrodes disposed on the cylindrical member operable to receive first and second electrical conductors, respectively. The first and second electrodes may be formed with titanium, chrome, tungsten, gold, and/or nickel. The first and second electrodes each may have a first surface proximate the first end of the cylindrical member and a second surface located between the first surface and the second end of the cylindrical member. The first surface may have a larger surface area than the second surface.

The apparatus may also include an electrical source and an electrical receiver in electrical communication with the first and second electrodes via the first and second electrical conductors, respectively, and a light source and a photodetector each in optical communication with the cylindrical member via the optical conductor. The light source may include a laser diode. An analog-to-digital converter and a processor are operable to distinguish between compositional components of a multiphase fluid surrounding the apparatus based on signals received from the electrical source, the electrical receiver, the light source, and the photodetector. The compositional components may include water and oil, and liquid and gas.

The present disclosure also introduces a downhole tool including a probe conveyable within a wellbore via a conveyance. The wellbore extends from a wellsite surface to a subterranean formation, and the conveyance includes an optical conductor and at least first and second electrical conductors. The probe includes an integrated sensor including a cylindrical member formed with an optically transparent material including a first end with a shaped tip and a second end operable to receive an optical conductor. The shaped tip may be substantially conical, biconical, conically rounded, or rounded. The optically transparent material may include sapphire. The optically transparent material may have an index of refraction greater than about 1.45. The integrated sensor also includes first and second electrodes disposed on the cylindrical member operable to receive the first and second electrical conductors, respectively. The first and second electrodes may be formed with titanium, chrome, tungsten, gold, and/or nickel. The first and second electrodes each may have a first surface proximate the first end of the cylindrical member and a second surface located between the first surface and the second end of the cylindrical member. The first surface may have a larger surface area than the second surface.

The downhole tool may further include the optical conductor, and a light source and a photodetector each in optical communication with the cylindrical member via the optical conductor. The light source may include a laser diode. The downhole tool may further include a processor operable to distinguish between gaseous and liquid components of a multiphase fluid surrounding the probe in the wellbore based on signals received from the light source and the photodetector. The light source and the photodetector may each be disposed at the wellsite surface.

The downhole tool may further include the first and second electrical conductors; and an electrical source and an electrical receiver each in electrical communication with the first and second electrodes via the first and second electrical conductors, respectively. The processor of the downhole tool is operable to distinguish between oil and water components of a multiphase fluid surrounding the probe in the wellbore based on signals received from the electrical source and the electrical receiver. The electrical source and the electrical receiver may each be disposed at the wellsite surface.

The processor of the downhole tool is also operable to distinguish between compositional components of a multiphase fluid surrounding the probe in the wellbore based on signals received from the electrical source, the electrical receiver, the light source, and the photodetector. The processor can distinguish between compositional components of the multiphase fluid including distinguishing between water and oil in the multiphase fluid, and distinguishing between gaseous and liquid phases of the multiphase fluid. An analog-to-digital converter of the downhole tool can convert measurement analog signals from the respective electrical receiver and photodetector into digital equivalents for the processing by the processor.

The systems and methods introduced in the present disclosure are susceptible to various modifications, variations, and/or enhancements without departing from the scope of the present disclosure. For example, different configurations can be employed for the integrated sensor to accommodate a downhole tool or other challenging environment. Accordingly, the present disclosure expressly encompasses all such modifications, variations, and enhancements within its scope.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same purposes and/or achieving the same advantages of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

What is claimed is:

1. A downhole tool, comprising:
   a probe conveyable within a wellbore via a conveyance, wherein the wellbore extends from a wellsite surface to a subterranean formation, wherein the conveyance comprises an optical conductor and at least first and second electrical conductors, wherein the probe includes an integrated sensor comprising:
   a cylindrical member including a side wall with the first and second electrical conductors disposed therein, a first end with a shaped tip and a second end operable to receive an optical conductor, wherein the side wall and the first end are formed with an optically transparent material; and first and second electrodes disposed on the side wall of the cylindrical member operable to receive the first and second electrical conductors, respectively.

2. The downhole tool downhole tool of claim 1 wherein the shaped tip is substantially conical.

3. The downhole tool of claim 1 further comprising:
   the optical conductor; and
   a light source and a photodetector each in optical communication with the cylindrical member via the optical conductor.

4. The downhole tool of claim 3 further comprising an analog-to-digital converter and a processor operable to distinguish between compositional components of a multiphase fluid surrounding the probe based on signals received from the electrical source, the electrical receiver, the light source, and the photodetector.

5. The downhole tool of claim 4 wherein the compositional components comprise water and oil.

6. The downhole tool of claim 4 wherein the compositional components comprise liquid and gas.

7. The downhole tool of claim 3 further comprising a processor operable to distinguish between gaseous and liquid components of a multiphase fluid surrounding the probe in the wellbore based on signals received from the light source and the photodetector.

8. The downhole tool of claim 3 wherein the light source and the photodetector are each disposed at the wellsite surface.

9. The downhole tool of claim 1 further comprising:
   the first and second electrical conductors; and
   an electrical source and an electrical receiver each in electrical communication with the first and second electrodes via the first and second electrical conductors, respectively.

10. The downhole tool of claim 9 further comprising a processor operable to distinguish between oil and water components of a multiphase fluid surrounding the probe in the wellbore based on signals received from the electrical source and the electrical receiver.

11. The downhole tool of claim 9 wherein the electrical source and the electrical receiver are each disposed at the wellsite surface.

12. The downhole tool of claim 9 further comprising:
    the optical conductor; and
    a light source and a photodetector each in optical communication with the cylindrical member via the optical conductor.

13. The downhole tool of claim 12 further comprising a processor operable to distinguish between compositional components of a multiphase fluid surrounding the probe in the wellbore based on signals received from the electrical source, the electrical receiver, the light source, and the photodetector.

14. The downhole tool of claim 13 wherein the processor is operable to:
    distinguish between water and oil in the multiphase fluid; and
    distinguish between gaseous and liquid phases of the multiphase fluid.

* * * * *